United States Patent
Azizian et al.

(10) Patent No.: US 11,389,268 B2
(45) Date of Patent: Jul. 19, 2022

(54) SYSTEM AND METHOD FOR ANATOMICAL MARKERS

(71) Applicant: INTUITIVE SURGICAL OPERATIONS, INC., Sunnyvale, CA (US)

(72) Inventors: Mahdi Azizian, Santa Clara, CA (US); Oliver Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 891 days.

(21) Appl. No.: 15/549,032

(22) PCT Filed: Feb. 4, 2016

(86) PCT No.: PCT/US2016/016521
§ 371 (c)(1),
(2) Date: Aug. 4, 2017

(87) PCT Pub. No.: WO2016/126914
PCT Pub. Date: Aug. 11, 2016

(65) Prior Publication Data
US 2018/0021102 A1    Jan. 25, 2018

Related U.S. Application Data

(60) Provisional application No. 62/112,416, filed on Feb. 5, 2015.

(51) Int. Cl.
*A61B 90/00* (2016.01)
*A61B 6/12* (2006.01)
(Continued)

(52) U.S. Cl.
CPC .......... *A61B 90/39* (2016.02); *A61B 1/00193* (2013.01); *A61B 5/055* (2013.01);
(Continued)

(58) Field of Classification Search
CPC .... A61B 2090/3966; A61B 2090/3941; A61B 90/39; A61B 5/055; A61B 5/064;
(Continued)

(56) References Cited

U.S. PATENT DOCUMENTS 5,469,847 A * 11/1995 Zinreich ................ G01R 33/58
156/145
8,032,204 B2   10/2011 Solar et al.
(Continued)

FOREIGN PATENT DOCUMENTS

WO   WO-2014093367 A1   6/2014

OTHER PUBLICATIONS

International Search Report and Written Opinion for Application No. PCT/US201616/016521, dated Jun. 1, 2016, 21 pages.
(Continued)

*Primary Examiner* — Rajeev P Siripurapu
*Assistant Examiner* — Milton Truong
(74) *Attorney, Agent, or Firm* — Haynes and Boone, LLP (57) ABSTRACT

A computer-assisted medical device includes a control unit, first and second articulated arms, a first imaging device mounted to the first articulated arm, and a medical tool mounted to the second articulated arm. The control unit obtains first images from a second imaging device using a first imaging modality, determines first coordinates of multi-modal anatomical markers secured to a patient based on the first images, obtains second images from the first imaging device using a second imaging modality, determines second coordinates of the multi-modal markers relative to the medical tool based on the second images, at least one of the
(Continued)

multi-modal markers including a body comprising a first region observable by the first imaging modality and a second region observable by the second imaging modality, and registers the medical tool to the patient based on the first and second coordinates and kinematic models of the first and second articulated arms.

7 Claims, 4 Drawing Sheets

(51) Int. Cl.
*A61B 5/055* (2006.01)
*A61B 1/00* (2006.01)
*A61B 5/00* (2006.01)
*A61B 5/11* (2006.01)
*A61B 6/02* (2006.01)
*A61B 6/00* (2006.01)
*A61B 5/06* (2006.01)

(52) U.S. Cl.
CPC ............ *A61B 5/064* (2013.01); *A61B 5/1127* (2013.01); *A61B 5/4504* (2013.01); *A61B 5/6878* (2013.01); *A61B 6/022* (2013.01); *A61B 6/12* (2013.01); *A61B 6/505* (2013.01); *A61B 6/487* (2013.01); *A61B 2090/3941* (2016.02); *A61B 2090/3954* (2016.02); *A61B 2090/3966* (2016.02)

(58) Field of Classification Search
CPC ......... A61B 5/1127; A61B 6/022; A61B 6/12; A61B 6/487; A61B 2090/3995
See application file for complete search history.

(56) References Cited

U.S. PATENT DOCUMENTS

| | | | |
|---|---|---|---|
| 8,041,459 B2 | 10/2011 | Sutherland et al. | |
| 8,798,716 B1* | 8/2014 | DeSena ................. | A61B 90/39 600/414 |
| 2006/0293581 A1* | 12/2006 | Plewes ............... | A61K 49/0419 600/407 |
| 2009/0161827 A1* | 6/2009 | Gertner .................. | A61F 9/008 378/65 |
| 2010/0063388 A1* | 3/2010 | Solar ..................... | A61B 90/39 600/426 |
| 2011/0105896 A1 | 5/2011 | Zagorchev et al. | |
| 2011/0130659 A1* | 6/2011 | Cinquin ................ | A61B 90/36 600/437 |
| 2013/0158565 A1* | 6/2013 | Anvari ................... | A61B 90/00 606/130 |
| 2013/0274596 A1* | 10/2013 | Azizian ................ | A61B 5/0071 600/424 |
| 2014/0051992 A1* | 2/2014 | Mostafavi ............. | A61B 6/032 600/424 |
| 2014/0058406 A1* | 2/2014 | Tsekos .................. | A61B 34/30 606/130 |
| 2014/0163736 A1* | 6/2014 | Azizian ................. | A61B 34/20 700/259 |
| 2017/0000380 A1* | 1/2017 | Gotman ................ | A61B 5/064 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2016/016521, dated Aug. 17, 2017, 15 pages.

* cited by examiner

SYSTEM AND METHOD FOR ANATOMICAL MARKERS

RELATED APPLICATIONS

This patent application is a U.S. National Stage patent application of International Patent Application No. PCT/US2016/016521 (filed on Feb. 4, 2016), the benefit of which is claimed, and claims priority to and the benefit of the filing date of U.S. Provisional Patent Application 62/112,416, entitled "SYSTEM AND METHOD FOR ANATOMICAL MARKERS," filed Feb. 5, 2015, each of which is incorporated by reference herein in its entirety.

TECHNICAL FIELD

The present disclosure relates generally to operation of devices with articulated arms and more particularly to anatomical markers for use with articulated arms.

BACKGROUND

More and more devices are being replaced with autonomous and semi-autonomous electronic devices. This is especially true in the hospitals of today with large arrays of autonomous and semi-autonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. When the articulated arms and/or the end effectors include redundant degrees of freedom (i.e., more than the six degrees of freedom typically associated with Cartesian x, y, and z positioning and roll, pitch, and yaw orientations), the articulated arms and/or the end effectors may provide extensive flexibility in adjusting to changes in patient size, position, and/or orientation as the articulated arms and/or the end effectors are used to support medical procedures. This is possible because the redundant degrees of freedom allow the articulated arms and/or the end effectors to be positioned so as to avoid collisions among themselves, the patient, and/or other devices and personnel in an operating room and/or interventional suite.

Many medical procedures call for high precision in both the positioning and/or orientation of medical tools and/or devices. For example, medical procedures involving percutaneous ablation (including RF, cryo, microwave, and/or other forms of ablation), percutaneous needle biopsy, bone drilling, bone screw placement, seed planting, medicine delivery, high magnification imaging, micro surgery, and/or the like often call for very precise control of not only the position of a medical device attached to an articulated arm and/or end effector, but control over the orientation and/or movement of the medical device within a patient's anatomy.

Traditional approaches to the problem have relied on the trained eye and the skilled and steady hands of medical personnel operating a respective medical device. However, even the most skilled and steady of practitioners may not be able to ensure adequate placement and/or orientation of the medical device, especially when high precision and/or accuracy are desired. This may be further complicated when the placement and/or orientation of the medical device is actively adjusted in synchronization with a physiological motion of the patient such as the physiological motions associated with respiration, heart beats, and/or the like.

To aid in the placement and/or orientation of medical devices during a procedure, medical personnel often use pre-operative images, such as images obtained via computed tomography (CT), magnetic resonance imaging (MRI), and/or the like to review the anatomy of a patient and to plan procedures. However, because the pose of the patient during the pre-operative imaging may be different from the pose during the procedure due to changes in joint positions, orientation on a patient table, and/or the like, it may not be a simple procedure to translate or map the anatomy observed in the pre-operative images with the anatomy as presented during the procedure.

To help maintain correlations and/or registration between the pre-operative images (and the associated plan) and intra-operative images taken during the procedure, the medical personnel may use one or more markers attached to the patient's anatomy that may be used to identify specific points on the patient's anatomy that may be located in both the pre-operative and intra-operative images so as to help the medical personnel match the pre-operative plan to the actual procedure. These markers may be used by the medical personnel and/or motion planning systems to help guide the medical devices used during the procedure.

One type of marker that may be used is an external marker, which is typically affixed to an exterior portion of the patient's anatomy. External markers typically operate in the visual and/or infrared spectrum so that they may be observed directly by the medical personnel or indirectly using imaging devices such as cameras, endoscopes, microscopes, and/or the like. These external markers may be active or passive. Active external markers may include a light emitting diode (LED) or other emitter and/or an electromagnetic emitter. The LED may be visually observed, whereas the electromagnetic emitter typically uses an electromagnetic field pattern detector. Passive external markers may include a reflector with light reflected from an additional light source being detected. And while external markers improve the ability to identify specific locations on the patient's anatomy, the external markers have several limitations that impact their usefulness. First, the external markers are typically attached to the exterior anatomy of the patient, which may not be rigidly related to the anatomy that is the target of the procedure. External placement generally limits use of the external markers with soft tissues of the patient, which may undesirably move relative to the target of the procedure. Second, the light-based external markers are limited to line of sight applications. And while the electromagnetic emitters may operate without line of sight between the emitters and a detector, the detector may be limited due to interference between the electromagnetic fields omitted by the electromagnetic emitters and/or electromagnetic fields from other medical devices in the vicinity of the patient. In many cases, distortions in the electromagnetic field caused by ferromagnetic material used in other medical devices within the electromagnetic fields, may be another source of inaccuracy in electromagnetic tracking systems.

Accordingly, it would be advantageous to develop systems and methods for improved markers that may be used to identify locations on a patient's anatomy.

SUMMARY

Consistent with some embodiments, an anatomical marker includes a first material observable to a first imaging modality and a second material observable to a second imaging modality. The first material is different from the second material. The first imaging modality is different from the second imaging modality. The first and second imaging modalities obtain their images without using light in a visible spectrum.

Consistent with some embodiments, a method of controlling motion of a medical tool includes obtaining one or more first images using a first imaging modality, determining first coordinates of one or more anatomical markers relative to an anatomy of a patient based on content of the first images, obtaining one or more second images using a second imaging modality, determining second coordinates of the one or more anatomical markers relative to the medical tool based on content of the second images, and registering the medical tool to the anatomy of the patient based on the first and second coordinates.

Consistent with some embodiments, a computer-assisted medical device includes a control unit comprising one or more processors, a first articulated arm comprising one or more first joints, a second articulated arm comprising one or more second joints, a first imaging device mounted to a distal end of the first articulated arm, and a medical tool mounted to a distal end of the second articulated arm. The control unit obtains one or more first images from a second imaging device using a first imaging modality, determines first coordinates of one or more anatomical markers relative to an anatomy of a patient based on content of the first images, obtains one or more second images using a second imaging modality, determines second coordinates of the one or more anatomical markers relative to the medical tool based on content of the second images, and registers the medical tool to the anatomy of the patient based on the first and second coordinates and kinematic models of the first and second articulated arms.

Consistent with some embodiments, a non-transitory machine-readable medium includes a plurality of machine-readable instructions which when executed by one or more processors associated with a medical device are adapted to cause the one or more processors to perform a method. The method includes obtaining one or more first images using a first imaging modality, determining first coordinates of one or more anatomical markers relative to an anatomy of a patient based on content of the first images, obtaining one or more second images using a second imaging modality, determining second coordinates of the one or more anatomical markers relative to a medical tool coupled to the medical device based on content of the second images, and registering the medical tool to the anatomy of the patient based on the first and second coordinates.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Computer-assisted systems with one or more articulated arms and/or end effectors provide great flexibility to the operating room and/or interventional suite. By providing computer control over the movement, position, and/or orientation of the articulated arms and/or the end effectors, it is possible for the computer-assisted system to provide significant advantages to both patients and medical personnel during medical procedures. In some examples, the computer-assisted systems may take advantage of information in both pre-operative and intra-operative images to help position and/or orient the end effectors and/or medical tools attached to the end effectors to desired positions within a patient's anatomy. In some examples, the computer-assisted systems may further provide guidance while a medical tool is being used during a procedure.

One possible use for a computer-assisted articulated arm and/or end effector is to help position, orient, and/or move a medical tool during a procedure. This may be useful when high precision and/or accuracy is desired during the procedure, such as during percutaneous ablation (including RF, cryo, microwave, and/or other forms of ablation), percutaneous needle biopsy, bone drilling, bone screw placement, seed planting, medicine delivery, high magnification imaging, micro surgery, and/or the like. To help provide the desired precision and/or accuracy, it is helpful for the personnel and/or the system controlling the medical tool at the distal end of the articulated arm and/or end effector to know the relative differences between the positions and/or orientations of the medical tool and the patient's anatomy by registering the medical tool with the patient. The pre-operative and/or intra-operative images are often used to help register the medical tool to the patient.

It would also be helpful to take fuller advantage, during the procedure, of the high precision and/or detailed information from the pre-operative images (e.g., the 3D information available from CT and MRI slices). To be useful, the pre-operative images are mapped and/or registered against intra-operative images by identifying one or more points on the patient's anatomy that may be located in both the pre-operative and intra-operative images. This is not always an easy task because the pose of the patient during the pre-operative imaging may be different from the pose during the procedure due to changes in joint positions, orientation on a patient table, and/or the like. This may be further complicated due to changes in the patient's anatomy during a procedure (e.g., while setting a bone, retracting an intervening anatomical structure, and/or the like) or due to a physiological motion of the patient (e.g., motion associated with respiration, heart beats, and/or the like).

One solution for registering both the medical tool to the patient and the pre-operative images with the intra-operative images is through the use of anatomical markers attached to the patient's anatomy. Anatomical markers, such as multi-modal markers may be useful in identifying locations on a patient's anatomy as observed by medical personnel and/or one or more medical imaging devices. Multi-modal markers are markers that are observable using more than one imaging approach. In some examples, a marker observable in both pre-operative images and intra-operative images may be used to locate the same anatomical points in both the pre-operative images and intra-operative images, thus often simplifying the registration of the pre-operative images with the intra-operative images, especially when the poses of the patient changes or the relative locations and/or orientations between portions of the anatomy change. In some examples, a marker observable in both pre-operative images and to intra-operative imaging devices, such as endoscopes, arthroscopes, surgical microscopes, and/or the like, may be used to register the medical tool to the patient.

Figure 1:
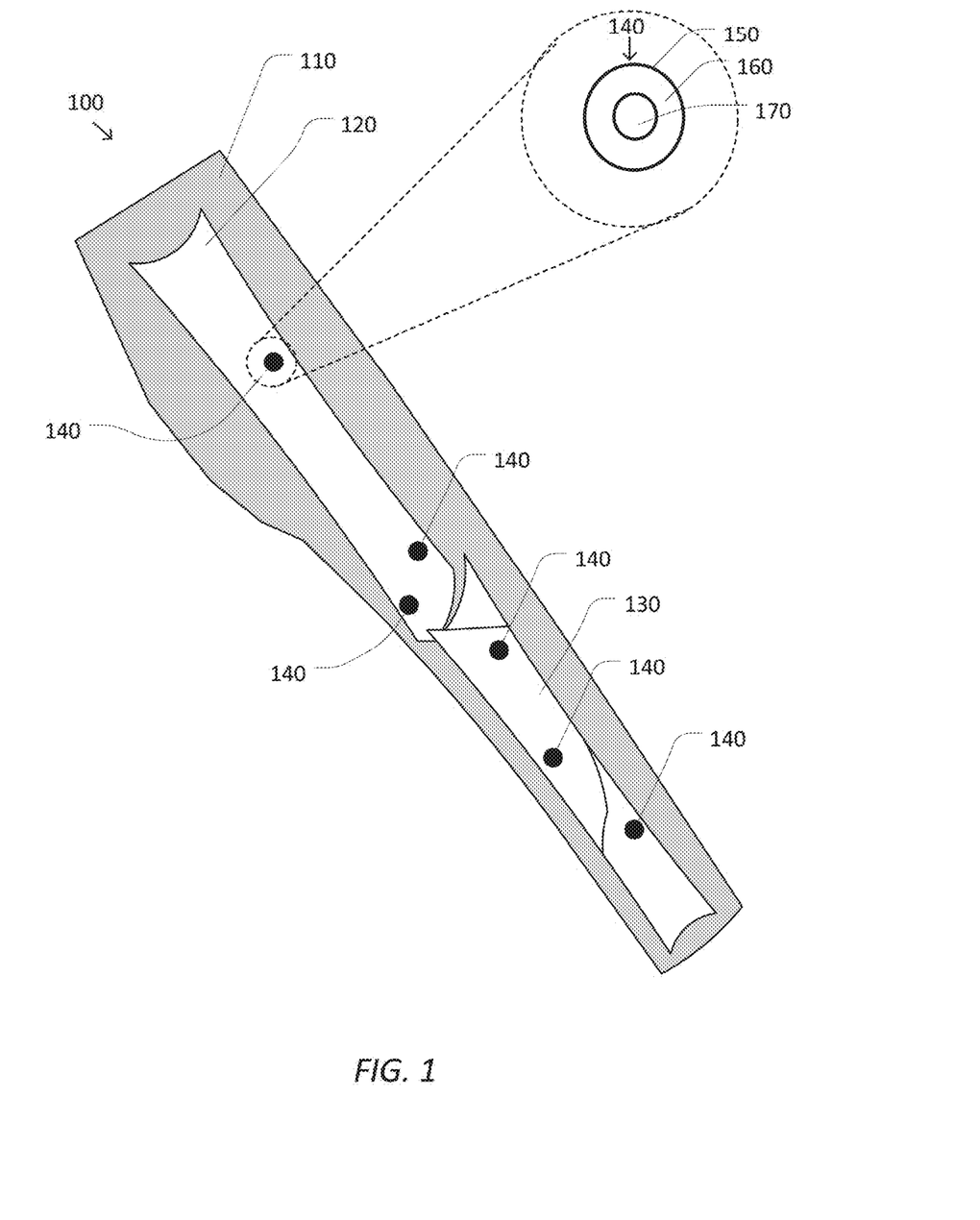
FIG. 1 is a simplified diagram showing the use of anatomical markers according to some embodiments.

FIG. 1 is a simplified diagram showing the use of anatomical markers according to some embodiments. FIG. 1 shows a simplified rendition of a patient's anatomy 100 depicting a significant injury to a bone. Soft tissue 110 surrounding the bone is shown in gray along with two major sections (an upper section 120 and a lower section 130) of the bone. As shown, there is a break between the upper section 120 and the lower section 130 with the upper section 120 and the lower section 130 being both separated and misaligned. The lower section 130 is further shown with a spiral fracture. Surgical repair of the bone may include setting the bone to provide correct positioning and orientation of the upper section 120 relative to the lower section 130 as well as the placement of one or more rods and/or plates that may be attached to the upper section 120 and lower section 130 of the bone using one or more bone screws.

To support intra-operative tracking of the relative locations of the upper section 120 and the lower section 130 of the bone, one or more fiducials or anatomical markers 140 may be attached to both the upper section 120 and the lower section 130 of the bone. By tracking the anatomical markers 140 during the procedure it is possible to monitor the proper setting of the bone as well as control precise and/or accurate placement of the rods, plates, bone screws, and/or any other treatment devices. To make the anatomical markers 140 as useful as possible, the anatomical markers 140 may be designed to be multi-modal markers which are observable by more than one type of imaging device.

In some embodiments, each of the anatomical markers 140 may include a transparent and hollow shell or shape filled with one or more materials observable by one or more imaging devices. In some examples, one or more the imaging devices may obtain their images without using light in the visible spectrum. In some examples, the visible spectrum may include wavelengths in a range between 390 nm and 700 nm. In some examples, each of the anatomical markers 140 may include one or more superabsorbent polymers for absorbing and/or containing the one or more materials observable by one or more imaging devices. In some examples, one or more of the superabsorbent polymers may be a hydrogel. In some examples, the one or more materials may include a mixture of fluids that is observable in an x-ray, fluoresces under appropriate excitation, is observable in a spectral range different from the excitation, and/or the like. In some examples, the one or more materials may include one or more contrast agents. In some examples, including a radio-opaque material, such as iodine, in the one or more materials makes the respective anatomical marker 140 observable in an x-ray. In some examples, including a fluorescent dye, such as indocyanine green (ICG), in the one or more materials allows the respective anatomical marker 140 to fluoresce when excited by specific wavelengths of light, such as near-infrared light. In some examples, including a gadolinium-based agent in the one or more materials makes the respective anatomical marker 140 observable in an MRI. In some examples, each of the anatomical markers 140 may be of different shapes and/or sizes to make it easier to tell one anatomical marker 140 from another. In some examples, the shapes may include spheres, circular cylinders, rectangular boxes, star-shaped cylinders, polygonal cylinders, letters, numbers, barcode patterns, chessboard patterns, and/or the like. In some examples, the shapes may be useful in observing an orientation of the anatomical makers relative to the patient's anatomy. In some examples, a rectangular box-shaped anatomical marker 140 may be aligned with a major axis of the upper section 120 and/or the lower section 130 of the bone. In some examples, anatomical markers 140 may fluoresce in response to different light wavelengths and the emitted light may be in different wavelengths to make it easier to tell one anatomical marker 140 from another. In some examples, a pattern among the anatomical markers may indicate an orientation of the patient's anatomy. In some examples, the anatomical markers 140 may be an unencapsulated free-form material such as a liquid or gel, which may be directly applied to the patient's anatomy.

A representative example of one of the anatomical markers 140 consistent with one or more embodiments is shown in the inset of FIG. 1. As shown in the inset, the anatomical marker 140 includes a body 150 divided into two regions. A first region 160 may be formed from and/or contain a first material that is observable via a first imaging modality and a second region 170 may be formed from and/or contain a second material different from the first material that is observable by a second imaging modality different from the first imaging modality. Note that while a relatively concentric arrangement of regions 160 and 170 is depicted for exemplary purposes, body 150 can incorporate any arrangement of regions and any number of regions. In some embodiments (not shown) other shapes and arrangements of the anatomical marker 140 are possible. In some examples, regions 160 and 170 may be combined into a single region formed from and/or containing both the first and second materials. In some examples, body 150 may have other shapes as previously described.

In some examples, each of the anatomical markers 140 may be affixed to the patient's anatomy using one or more bio-adhesives in the form of a resin, a paste, a paint-like adhesive, and/or the like. In some examples, the one or more adhesives may be applied by brushing and/or spraying. In some examples, when the anatomical markers 140 are the free-form material, the anatomical markers 140 may be injected, brushed, and/or sprayed directly on the patient's anatomy. In some embodiments, anatomical markers 140 may include integrated or detachable attachment features (e.g., threads, clamps, claws, spikes) that enable direct attachment to the desired anatomical feature(s).

Although FIG. 1 depicts the anatomical markers affixed to a rigid anatomical structure, such as the upper section 120 and the lower section 130 of the bone, other placement locations for the anatomical markers 140 are possible. In some examples, the anatomical markers 140 may be affixed to soft tissues of the patient's anatomy. In some examples, the anatomical markers may be affixed to the medical tools, the end effectors, and/or the articulated arms of the computer-assisted medical device to aid in observation of the positions and/or orientations of the medical tools, the end effectors, and/or the articulated arms in the same and/or different images used to observe the patient's anatomy.

As discussed above and further emphasized here, FIG. 1 is merely an example, which should not unduly limit the scope of the claims. One of ordinary skill in the art would recognize many variations, alternatives, and modifications. According to some embodiments, the anatomical markers may be used for procedures and to address other medical issues than those shown in FIG. 1. In some examples, the anatomical markers may be used to help ensure proper bone alignment during a spine or other bone fusion where two or more vertebrae and/or two or more bone plates are joined together.

Figure 2:
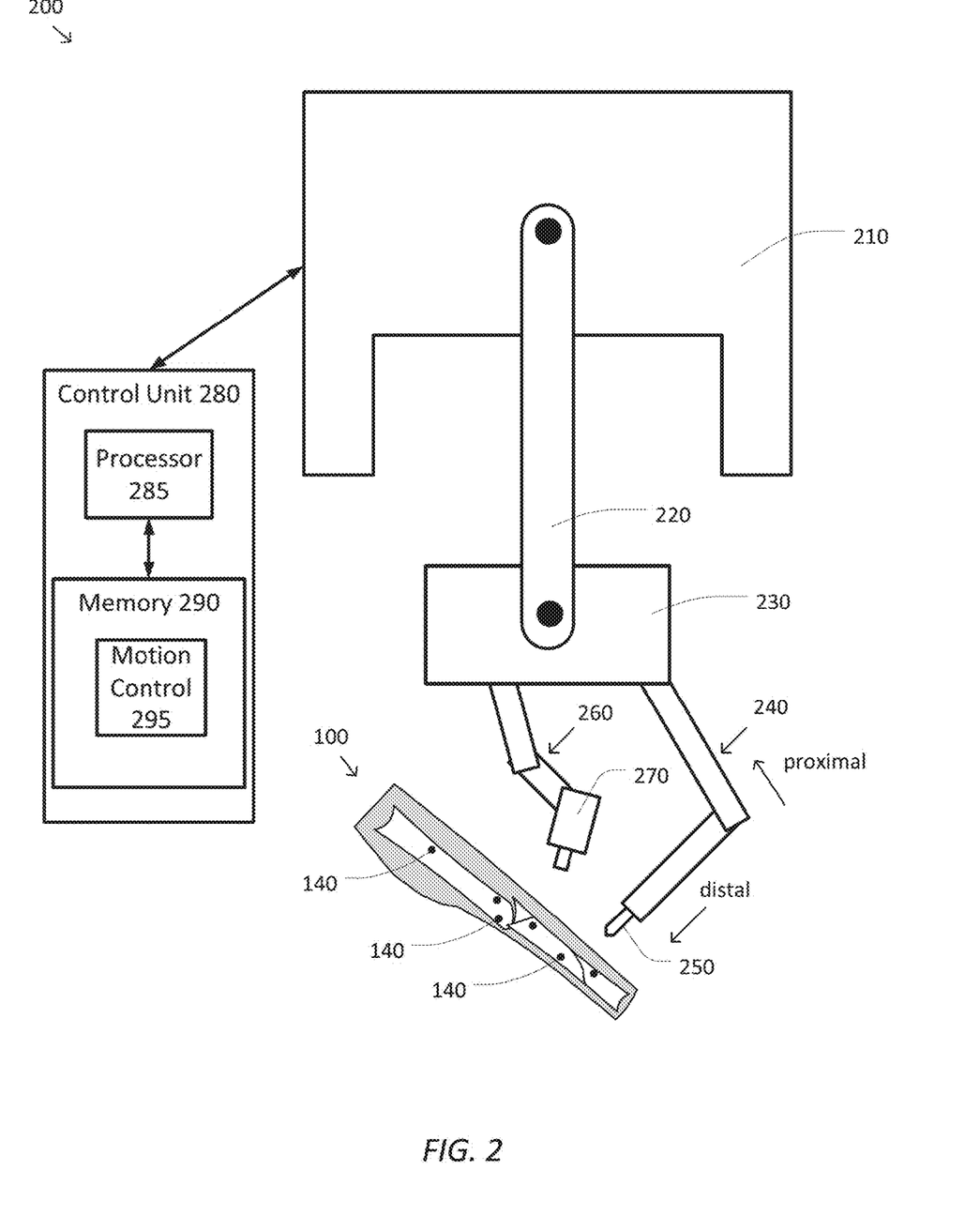
FIG. 2 is a simplified diagram of a computer-assisted system according to some embodiments.

FIG. 2 is a simplified diagram of a computer-assisted system 200 according to some embodiments. As shown in FIG. 2, computer-assisted system 200 includes a computer-assisted medical device supporting multiple articulated arms. In some embodiments, the computer-assisted medical device and an operator workstation (not shown) may correspond to a da Vinci® Surgical System commercialized by Intuitive Surgical, Inc. of Sunnyvale, Calif. The computer-assisted medical device includes a base 210. In some examples, base 210 may include one or more wheels and/or may be mounted on a track to facilitate positioning of the computer-assisted medical device within an operating room, interventional suite, and/or adjacent to a patient table. To facilitate positioning of the articulated arms of the computer-assisted medical device, a set-up structure 220 may be mounted on base 210. The set-up structure 220 may include one or more joints and/or links that may be used to adjust a position, orientation, and/or height of an articulated arm gantry 230. In some examples, gantry 230 may be positioned over a patient table. In some examples, set-up structure 220 may further include one or more sensors and/or the like to allow computer-assisted system 200 to determine a forward and/or inverse kinematic transform characterizing the position and/or orientation of gantry 230 relative to base 210. In some examples, set-up structure 220 may further include one or more actuators and/or the like to allow computer-assisted system 200 to change the position and/or orientation of gantry 230 relative to base 210 and set-up structure 220.

Attached to gantry 230 are several articulated arms 240 and 260. And although FIG. 2 shows two articulated arms 240 and 260 attached to gantry 230, other configurations may include additional articulated arms. Each of the articulated arms 240 and 260 may include one or more joints and links between the proximal end attached to gantry 230 and the distal end to which a respective end effector, imaging device, medical tool, and/or the like are attached. In some examples, each of the articulated arms 240 and 260 may further include one or more sensors and/or the like to allow computer-assisted system 200 to determine a forward and/or inverse kinematic transform characterizing the position and/or orientation of the distal end of the respective articulated arm 240 and/or 260 relative to gantry 230. In some examples, each of the articulated arms 240 and 260 may further include one or more sensors for determining forces and/or torques being applied to the joints and/or links of the respective articulated arm 240 and/or 260. In some examples, each of the articulated arms 240 and 260 may further include one or more actuators and/or the like to allow computer-assisted system 200 to change the position and/or orientation of respective end effectors at the distal ends of each of the articulated arms 240 and 260 relative to gantry 230.

As shown in FIG. 2, a medical tool 250 is attached to the distal end of articulated arm 240. Medical tool 250 may be any suitable tool for performing part of a medical procedure on a patient. In some examples, medical tool 250 may include instruments for making incisions, cauterizing, retracting, suturing, ablating, biopsying, drilling, placing bone screws, planting seeds, delivering medicine, and/or the like. An imaging device 270 may be attached to the distal end of articulated arm 260. In some examples, imaging device 270 may be an endoscope, an arthroscope, a surgical microscope, and/or the like. In some examples, imaging device 270 may provide one or more images of a patient's anatomy.

Also shown in FIG. 2 is the representative patient's anatomy 100 from FIG. 1. Imaging device 270 may be used to acquire one or more images of the patient's anatomy 100 including one or more of the anatomical markers 140 using one or more of the modalities of the respective anatomical markers 140. In some examples, the one or more images may further include portions of the medical tool 250 and/or the articulated arm 240. Using the one or more images, an operator of the computer-assisted system 200 and/or the computer-assisted system 200 may operate the medical tool 250 with high precision and/or accuracy.

As further shown in FIG. 2, the computer-assisted medical device is coupled to a control unit 280 via an interface. The interface may include one or more cables, connectors, and/or buses and may further include one or more networks with one or more network switching and/or routing devices. Control unit 280 includes a processor 285 coupled to memory 290. Operation of control unit 280 is controlled by processor 285. And although control unit 280 is shown with only one processor 285, it is understood that processor 285 may be representative of one or more central processing units, multi-core processors, microprocessors, microcontrollers, digital signal processors, field programmable gate arrays (FPGAs), application specific integrated circuits (ASICs), and/or the like in control unit 280. Control unit 280 may be implemented as a stand-alone subsystem and/or board added to a computing device or as a virtual machine. In some embodiments, control unit 280 may be included as part of an operator workstation (not shown) for allowing medical personnel to control and/or operate computer-assisted system 200. In some examples, control unit 280 may be operated separately from, but in coordination with the operator workstation.

Memory 290 may be used to store software executed by control unit 280 and/or one or more data structures used during operation of control unit 280. Memory 290 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 290 includes a motion control application 295 that may be used to support autonomous and/or semi-autonomous control of computer-assisted system 200. Motion control application 295 may include one or more application programming interfaces (APIs) for receiving position, motion, and/or other sensor information from the sensors in set-up structure 220, the articulated arms 240 and/or 260, the medical tool 250, and/or the imaging device 270 as will be discussed in further detail below. In some examples, motion control application 295 may receive one or more pre-operative images, intra-operative images, images from imaging device 270, and/or the like as will be discussed in further detail below. In some examples, motion control application 295 may support the autonomous and/or semi-autonomous motion of articulated arms 240 and/or 260 to help position and/or orient the medical tool 250 as will be discussed in further detail below. In some examples, motion control application 295 may also exchange position, motion, and/or collision avoidance information with other control units regarding other devices, and/or planning and/or assisting in the planning of motion for computer-assisted system 200, articulated arms 240 and/or 260, medical tool 250, imaging device 270, and/or the like. And although motion control application 295 is depicted as a software application, motion control application 295 may be implemented using hardware, software, and/or a combination of hardware and software.

Figure 3:
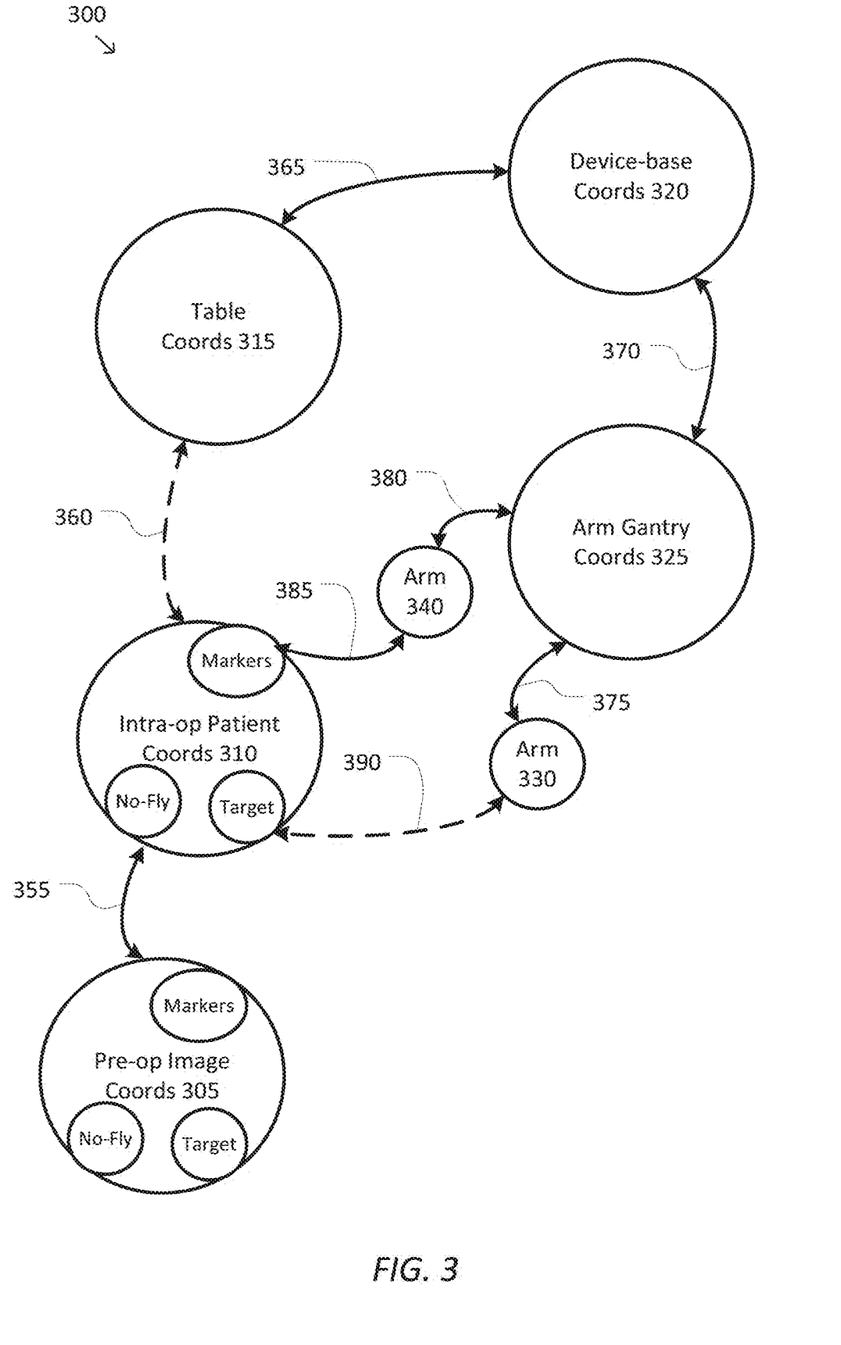
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. In some embodiments, before a medical procedure is performed, it is common for one or more pre-operative images to be obtained. In some examples, these pre-operative images may include a series of tomographic images that may be used to develop a three-dimensional model of the patient's anatomy. In some examples, the pre-operative images may be taken via CT, MRI, and/or the like. In some examples, medical personnel may review the pre-operative images to develop a plan for a medical procedure that may include identifying desired locations for one or more anatomical markers, and/or one or more targets of a procedure (e.g., positions for incisions, sutures, needle ablation, biopsy, seeds, drilling points, bone screws, and/or the like). In some examples, the plan may also identify one or more no-fly zones that may be used to protect patient anatomy during the medical procedure. In some examples, the pre-operative images, as well as the anatomical markers, targets, and/or no-fly zones may be established in a pre-operative image coordinate system 305. In some examples, the pre-operative images may also detect the locations of one or more previously placed anatomical markers. In some examples, the pre-operative image coordinate system 305 may be determined in part by a coordinate system and/or one or more kinematic models associated with the one or more imaging devices taking the pre-operative images.

In some embodiments, once the patient is positioned and oriented for the medical procedure, one or more intra-operative images may be obtained to determine the position and/or orientation of the patient for the medical procedure. In some examples, the intra-operative images may include two or more x-rays obtained along non-parallel axes. In some examples, the non-parallel axes may have an angular separation of at least 30 degrees. In some examples, the x-ray images may be lateral and anterior-posterior images of the patient. In some examples, the intra-operative images may use other imaging technology that identifies three-dimensional information and may include ultrasound, bi-plane fluoroscopy, stereoscopic visual and/or fluorescence imaging, range imaging, and/or the like. In some examples, the intra-operative images may be used to locate the positions of the one or more anatomical markers affixed to the patient's anatomy. In some examples, an intra-operative patient coordinate system 310 may be determined in part by a coordinate system and/or one or more kinematic models associated with the one or more imaging devices taking the intra-operative images.

In some embodiments, medical personnel may review the intra-operative images to determine positions of the targets identified as part of the plan using the pre-operative images. In some examples, one or more no-fly zones may also be identified in the intra-operative images. In some examples, positions of one or more anatomical markers and/or identified anatomical features may be located using the intra-operative images. In some examples, the intra-operative images, as well as the targets, no-fly zones, features, and/or anatomical markers may be established in the intra-operative patient coordinate system 310.

In some embodiments, the patient may be located on a patient table that may be positioned and/or oriented by medical personnel. In some examples, a height of the patient table above the floor may be adjusted. In some examples, an orientation of the patient table may be adjusted along one or more roll, pitch, yaw, and/or the like axes. In some examples, the position and/or orientation of the patient table may be established in a table coordinate system 315.

In some embodiments, a computer-assisted medical device, such as the computer-assisted medical device of FIG. 2, may be used during the medical procedure. In some examples, the position and/or orientation of a base of the computer-assisted medical device may be adjusted relative to the patient table. In some examples, the computer-assisted medical device may be established in a device-base coordinate system 320.

In some embodiments, the computer-assisted medical device may include a set-up structure, such as set-up structure 220, to adjust a position and orientation of a gantry to which one or more articulated arms are attached. In some examples, the gantry may be similar to gantry 230. In some examples, the gantry may be established in an arm gantry coordinate system 325.

In some embodiments, a plurality of articulated arms may be attached to the gantry. Each of the articulated arms may include one or more joints and/or links with the joints and/or links establishing a coordinate system 330 and/or 340 at a distal end of each of the articulated arms and/or an end effector at the distal end of a respective articulated arm. In some examples, the articulated arms associated with arm coordinate systems 330 may correspond to articulated arm 240 and the articulated arm associated with arm coordinate system 340 may correspond to articulated arm 260.

In some embodiments, a medical tool may be coupled to the distal end of the articulated arm associated with arm coordinate system 330. In some examples, the position and/or orientation of the medical tool in the arm coordinate system 330 may be determined.

In some embodiments, an imaging device may be coupled to the distal end of the articulated arm associated with arm coordinate system 340. In some examples, the imaging device may be an endoscope, an arthroscope, a surgical microscope, and/or the like. In some examples, the imaging device may include stereoscopic and/or other three-dimensional positioning capabilities for mapping observed images to arm coordinate system 340.

In some embodiments, kinematic modeling and/or one or more registration processes may be used to establish the kinematic relationships between the various coordinate systems 305-340. In some examples, the kinematic modeling and/or registration processes may be used to establish transformation matrices between the various coordinate systems 305-340 to permit the forward and/or reverse mapping of positions and/or orientations in one of the coordinate systems 305-340 to another of the coordinate systems 305-340.

In some embodiments, a registration process may be used to determine a pre-operative to intra-operative kinematic relationship 355 between the pre-operative coordinate system 305 and the intra-operative patient coordinate system 310. In some examples, the registration process may include identifying common image elements in the pre-operative and intra-operative images (e.g., unique and/or unusual anatomical features, anatomical markers, and/or the like), locating the common image elements in both the pre-operative image and intra-operative patient coordinate systems 305, 310, and using the differences between the positions and/or orientations of the common image elements to determine the translations, scales, and/or rotations between the pre-operative image coordinate system 305 and the intra-operative coordinate system 310. The translations, scales, and/or rotations may be used to determine the pre-operative to intra-operative kinematic relationship 355. In some examples, the pre-operative to intra-operative kinematic relationship 355 may be used to transform the anatomical marker locations, targets, and/or no-fly zones identified during the pre-operative plan from the pre-operative image coordinate system 305 to the intra-operative patient coordinate system 310. In some examples, the pre-operative to intra-operative kinematic relationship 355 may include multiple transformations that apply to sub-regions within the pre-operative and intra-operative coordinate systems 305 and 310 to account for changes in the patient's anatomy between a pose used for the pre-operative images and the pose used for the intra-operative images. In some examples, the sub-regions may account for changes in positions of the patient's joints, vertebrae, and/or the like between the pre-operative and intra-operative poses.

In some embodiments, a patient to table kinematic relationship 360 between the patient (i.e., the intra-operative patient coordinate system 310) and the patient table (i.e., the table coordinate system 315) may not be directly determined. However, a closed kinematic chain may be used to determine the patient to table kinematic relationship 360 as is discussed in further detail below.

In some embodiments, a table to device-base kinematic relationship 365 may be determined using a registration process between the patient table and the computer-assisted medical device. Methods and approaches for establishing the table to device-base kinematic relationship are described in greater detail in U.S. Patent Application No. 61/954,538 (filed Mar. 17, 2014) (entitled "Methods and Systems for Tele-Surgical Table Registration"), which is hereby incorporated by reference for all purposes.

In some embodiments, a set-up structure kinematic relationship 370 between the device-base coordinate system 320 and the arm gantry coordinate system 325 may be determined by using one or more kinematic models of the set-up structure coupling the device base to the gantry. In some examples, one or more sensors located in the set-up structure may be used to determine the coordinate transformation associated with the set-up structure kinematic relationship 370. In some examples, the set-up structure kinematic relationship 370 may be updated as the gantry is moved to different positions and/or orientations relative to the device base coordinate system 320.

In some embodiments, an articulated arm kinematic relationship 375 between the arm gantry coordinate system 325 and the articulated arm coordinate system 330 may be determined by using one or more kinematic models of the articulated arm and/or the end effector coupling the gantry to a distal end of the articulated arm and/or the end effector. In some examples, one or more sensors located in the articulated arm and/or the end effector may be used to determine the coordinate transformation associated with the articulated arm kinematic relationship 375. In some examples, the articulated arm kinematic relationship 375 may be updated as the articulated arm and/or the end effector is moved to different positions and/or orientations relative to the arm gantry coordinate system 325.

In some embodiments, an articulated arm kinematic relationship 380 between the arm gantry coordinate system 325 and the articulated arm coordinate system 340 may be determined by using one or more kinematic models of the articulated arm and/or end effector coupling the gantry to a distal end of the articulated arm and/or end effector. In some examples, one or more sensors located in the articulated arm and/or end effector may be used to determine the coordinate transformation associated with the articulated arm kinematic relationship 380. In some examples, the articulated arm kinematic relationship 380 may be updated as the articulated arm and/or end effector are moved to a different position and/or orientation relative to the gantry coordinate system 325.

In some embodiments, when an imaging device coupled to the articulated arm associated with the articulated arm coordinate system 340 is able to observe the features and/or anatomical markers located in the intra-operative patient coordinate system 310, it is possible to determine a patient kinematic relationship 385 between the articulated arm coordinate system 340 and the anatomy of the patient. In some examples, image processing of one or more images obtained by the imaging device may be used to determine positions and/or orientations of the features and/or anatomical markers on the anatomy of the patient in articulated arm coordinate system 340 and, thus, determine the patient kinematic relationship 385. In some examples, the positions and/or orientations of the anatomical markers, targets, and/or no-fly zones in the intra-operative patient coordinate system 310 may be mapped to the articulated arm coordinate system 340 by using the patient kinematic relationship 385.

In some embodiments, a closed kinematic chain through the intra-operative patient coordinates 310, patient kinematic relationship 385, articulated arm coordinate system 340, articulated arm kinematic relationship 380, arm gantry coordinate system 325, articulated arm kinematic relationship 375, articulated arm coordinate system 330, may be used to determine a medical tool to target kinematic relationship 390 by suitable application of the inverse and forward kinematic relationships. In some examples, the medical tool to target kinematic relationship 390 may be used to quickly convert the position and orientation of the medical tool in the articulated arm coordinate system 330 to the intra-operative patient coordinate system 310 so as to support positioning and alignment of the medical tool with the target while avoiding the no-fly zones.

In some embodiments, the patient to table kinematic relationship 360 may also be determined using the closed kinematic loop through the table to device-base kinematic relationship 365, the set-up kinematic relationship 370, the articulated arm kinematic relationship 380, and the patient kinematic relationship 385.

In some embodiments, the various kinematic relationships 355-390 may also be used to support collision avoidance when using the computer-assisted medical device. In some examples, the kinematic relationships (e.g., kinematic relationships 375 and/or 380) may be used to help avoid collisions between the various articulated arms, such as between the articulated arm holding the medical tool and the articulated arm holding the imaging device used to establish the patient kinematic relationship 385. In some examples, the kinematic relationships (e.g., kinematic relationships 360-390) may be used to prevent the articulated arms from entering the no-fly zones in the intra-operative patient coordinate system 310 and/or the patient table.

Figure 4:
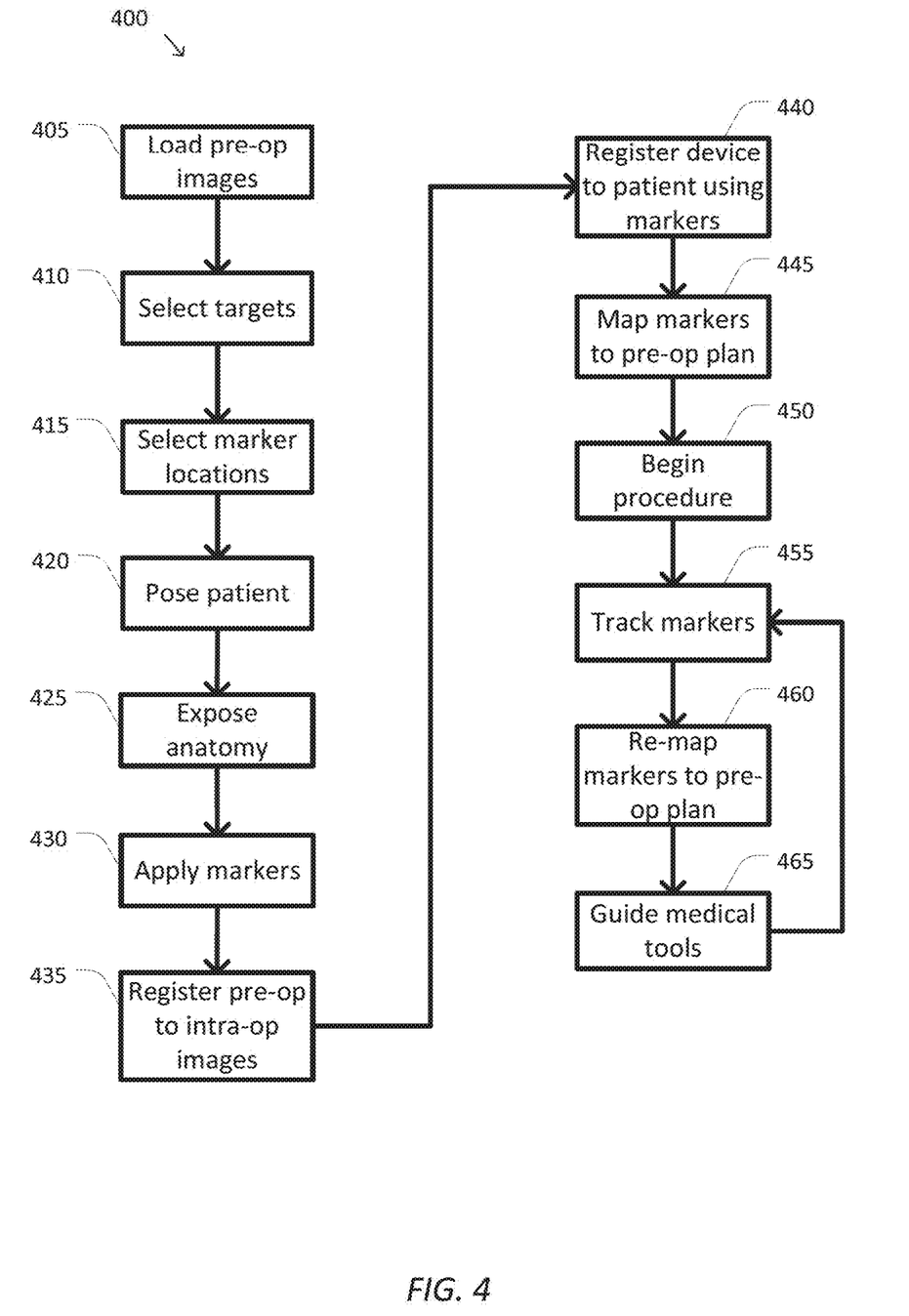
FIG. 4 is a simplified diagram of a method of performing a medical procedure with the assistance of anatomical markers according to some embodiments In the figures, elements having the same designations have the same or similar functions.

FIG. 4 is a simplified diagram of a method 400 of performing a medical procedure with the assistance of anatomical markers according to some embodiments. One or more of the processes 405-465 of method 400 may be implemented, at least in part, in the form of executable code stored on non-transient, tangible, machine readable media that when run by one or more processors (e.g., the processor 285 in control unit 280) may cause the one or more processors to perform one or more of the processes 405-465. In some embodiments, the method 400 may be performed by an application, such as motion control application 295. In some embodiments, variations in the processes 405-465 are possible, such as performing only certain of the processes and/or one or more of the processes simultaneously and/or in different orders, as would be understood by one of ordinary skill in the art.

At a process 405, one or more pre-operative images are loaded. In some embodiments, a surgical plan is determined upon review of the one or more pre-operative images. In some examples, the one or more pre-operative images may be images of a desired portion of a patient's anatomy. In some examples, the one or more pre-operative images may include one or more slices and/or other three-dimensional information of the patient's anatomy. In some examples, the one or more pre-operative images may be obtained from a tomographic imaging device such as a CT, MRI, and/or similar imaging device. In some examples, the one or more pre-operative images may be associated with a pre-operative image coordinate system, such as pre-operative image coordinate system 305. During process 405, at least one of the pre-operative images is loaded for display to medical personnel.

At a process 410, targets are selected. In some embodiments, the medical personnel may review the one or more pre-operative images loaded during process 405 to determine one or more targets for a medical procedure. In some examples, the one or more targets may be selected using a pointing device on the pre-operative image loaded during process 405. In some examples, each of the one or more targets may be associated with a portion of a patient's anatomy that is to be the subject of an incision, cauterization, suturing, percutaneous ablation including RF, cryo, microwave, and/or other forms of ablation), percutaneous needle biopsy, bone drilling, bone screw placement, seed planting, medicine delivery, high magnification imaging, micro surgery, and/or the like. In some examples, the one or more targets may be located within the pre-operative image coordinate system.

At a process 415, one or more anatomical marker locations are selected. In some embodiments, the medical personnel may further review the one or more pre-operative images loaded during process 405 to determine locations of one or more existing anatomical markers and/or locations for placement of one or more additional anatomical markers. In some examples, the one or more anatomical marker locations may be selected using a pointing device on the pre-operative image loaded during process 405. In some examples, the one or more anatomical markers may be used to mark boundaries of one or more areas of interest, such as margins of a tumor to be removed. In some examples, the one or more anatomical marker locations may be the targets identified during process 410. In some examples, the locations of the one or more anatomical markers may be used to establish one or more no-fly zones within the one or more pre-operative images. In some examples, the one or more no-fly zones may correspond with one or more regions of the patient's anatomy, which are to be avoided by a computer-assisted surgical system and/or one or more medical tools. In some examples, the one or more anatomical marker locations may be located within the pre-operative image coordinate system.

At a process 420, the patient is posed. In some embodiments, the patient may be prepared for a medical procedure and then posed on a patient table. In some examples, once the patient is posed, the particular pose may be associated with an intra-operative patient coordinate system, such as intra-operative patient coordinate system 310. In some examples, the patient table may be associated with a table coordinate system, such as table coordinate system 315.

At a process 425, one or more locations on the anatomy of the patient are exposed. In some examples, one or more incisions may be made on the patient to provide access to the one or more anatomical marker locations selected during process 415. In some examples, one or more portions of the patient's anatomy may also be retracted away from one or more of the anatomical marker locations selected during process 415. In some examples, when one or more of the anatomical markers are being placed using a needle and/or other minimally invasive anatomical marker placement device, the corresponding anatomical marker locations may be exposed without the use of incisions and/or retraction.

At a process 430, the anatomical markers are applied. In some examples, an anatomical marker, such as any of the anatomical markers, 140, may be applied to each of the locations selected during process 415. In some examples, anatomical markers of different shapes and/or sizes may be applied to each of the selected locations. In some examples, the shape and/or size selected for each of the anatomical markers may be determined based on the surgical plan determined during processes 405-415. In some examples, one or more of the anatomical markers may be applied so that the respective anatomical marker maintains a desired orientation relative to the portion of the patient's anatomy to which it is applied. In some examples, each of the one or more anatomical markers may be applied to rigid tissue and/or soft tissue. In some examples, the shape, size, and/or orientation of each of the anatomical markers may be recorded for later use when additional images are obtained to track the anatomical markers.

Depending upon the type, shape, size, and/or purpose of the one or more anatomical markers, the one or more anatomical markers may be applied using one of numerous techniques. In some examples, one or more of the anatomical markers may be applied using one or more bio-adhesives. In some examples, the one or more bio-adhesives may be in the form of a resin, a paste, a paint-like adhesive, and/or the like. In some examples, the one or more adhesives may be applied by brushing and/or spraying. In some examples, the one or more bio-adhesives may be applied to the selected location on the patient's anatomy before the corresponding anatomical marker is applied. In some examples, the one or more bio-adhesives may be applied to the corresponding anatomical marker before the corresponding anatomical marker is applied to the selected location of the patient's anatomy. In some examples, the one or more bio-adhesives may be applied to both the selected location of the patient's anatomy and the corresponding anatomical marker before the corresponding anatomical marker is applied. In some examples, the anatomical markers may include integrated or detachable attachment features. In some examples, when one or more of the anatomical markers are composed of a free-form material, the corresponding anatomical markers may be injected, brushed, and/or sprayed directly on the selected locations of the patient's anatomy. In some examples, one or more of the anatomical markers may be used to trace one or more boundaries and/or one or more no-fly zones on the patient's anatomy.

In some examples, one or more of the anatomical markers may be applied manually by medical personnel. In some examples, one or more of the anatomical markers may be applied autonomously and/or semi-autonomously using one or more anatomical marker application tools attached to and/or manipulated by an articulated arm and/or end effector of a computer-assisted medical device.

At a process 435, the one or more pre-operative images are registered to one or more intra-operative images. In some embodiments, once the patient is posed for the medical procedure during process 420 and/or the one or more markers are applied during process 430, one or more intra-operative images may be obtained to determine the position and/or orientation of the patient for the medical procedure. In some examples, the intra-operative images may include two or more x-rays obtained along non-parallel axes. In some examples, the non-parallel axes may have an angular separation of at least 30 degrees. In some examples, the x-ray images may be lateral and anterior-posterior images of the patient. In some examples, the intra-operative images may use other imaging technology that identifies three-dimension information and may include ultrasound, bi-plane fluoroscopy, stereoscopic visual and/or fluorescence imaging, range imaging, and/or the like. In some examples, the one or more intra-operative images may be associated with the intra-operative patient coordinate system.

In some examples, the registration may be used to determine a pre-operative to intra-operative kinematic relationship, such as the intra-operative kinematic relationship 355 between the pre-operative coordinate system 305 and the intra-operative patient coordinate system 310. In some examples, the registration process may include automated and/or semi-automated identification of one or more common image elements in the one or more pre-operative images and the one or more intra-operative images (e.g., one or more unique and/or unusual anatomical features, the one or more anatomical markers, and/or the like), locating the one or more common image elements in both the pre-operative image and intra-operative patient coordinate systems, and using the differences between the positions and/or orientations of the one or more common image elements to determine the translations, scales, and/or rotations between the pre-operative image coordinate system and the intra-operative patient coordinate system. The translations, scales, and/or rotations may be used to determine the pre-operative to intra-operative kinematic relationship. In some examples, the pre-operative to intra-operative kinematic relationship may be used to transform the one or more targets selected during process 410, and/or the one or more anatomical marker locations selected during process 415 from the pre-operative image coordinate system to the intra-operative patient coordinate system. In some examples, medical personnel may update the one or more target positions and/or the one or more anatomical marker locations based on the intra-operative patient pose. In some examples, the pre-operative to intra-operative kinematic relationship may include multiple transformations that apply to sub-regions within the pre-operative and intra-operative coordinate systems to account for changes in the patient's anatomy between a pose used for the one or more pre-operative images loaded during process 405 and the pose used for the one or more intra-operative images. In some examples, the sub-regions may account for changes in positions of the patient's joints, and/or the like between the pre-operative and intra-operative poses.

At a process 440, the computer-assisted medical device is registered to the patient using the one or more anatomical markers. In some examples, an imaging device may be used to obtain one or more images of the patient's anatomy and/or one or more of the anatomical markers on the patient's anatomy. In some examples, the one or more images may be obtained using an imaging device, such as imaging device 270, attached to the distal end of an articulated arm and/or end effector that may be positioned and/or oriented as desired either internally and/or externally to the patient. In some examples, the one or more images may be obtained using a stereoscopic endoscope, arthroscope, surgical microscope, and/or the like. In some examples, the one or more stereoscopic images may be used to determine a position and/or orientation of the one or more anatomical markers within a coordinate system of the imaging device, such as the arm coordinate system 340. In some examples, the shape, size, and/or orientation of the anatomical markers recorded during process 430 may be used to differentiate between two or more anatomical markers that appear in the same one or more images.

In some examples, the registration may be used to determine a patient to computer-assisted medical device kinematic relationship, such as the patient kinematic relationship 385 between the intra-operative coordinate system 310 and the articulated arm coordinate system 340. In some examples, the registration process may include automated and/or semi-automated identification of the one or more anatomical markers in the one or more computer-assisted medical device based images and the one or more intra-operative and/or one or more pre-operative images and using the differences between the positions and/or orientations of the one or more anatomical markers to determine the translations, scales, and/or rotations between the intra-operative patient coordinate system and the articulated arm coordinate system. The translations, scales, and/or rotations may be used to determine the patient to computer-assisted medical device kinematic relationship. In some examples, the patient to computer-assisted medical device kinematic relationship may be used to transform the one or more targets selected during process 410 from the intra-operative patient coordinate system to the articulated arm coordinate system. In some examples, additional coordinate systems (e.g., coordinates systems 320, 325, and/or 330) and their kinematic relationships (e.g., kinematic relationships 370, 375, and/or 380) may be used to transform the one or more targets selected during process 410 from the intra-operative patient coordinate system to one or more of the additional coordinate systems.

At a process 445, the one or more anatomical markers are mapped to the pre-operative surgical plan. Using the pre-operative to intra-operative kinematic relationship determined during process 435 and the patient kinematic relationship determined during process 440, the one or more anatomical markers are mapped from the articulated arm to the pre-operative coordinate system to establish the kinematic relationship between the computer-assisted medical device and its articulated arms and/or end effectors and the pre-operative coordinate system. In some examples, medical personnel may update the one or more target positions and/or the one or more marker locations during this mapping process to account for possible changes in the one or more anatomical locations relative to the locations selected for them during process 415. In some examples, the mapping between the articulated arm coordinate system and the pre-operative coordinate system allows the positions and/or orientations of the medical tools being operated by the computer-assisted medical device to be determined relative to the surgical plan so that the medical tools may be operated according to the surgical plan.

At a process 450, the procedure is begun. Once the kinematic relationships between the pre-operative coordinate system and the intra-operative patient coordinate system and the coordinate systems of the computer-assisted medical device are known by registering, the procedure may begin.

At a process 455, the one or more anatomical markers are tracked. In some examples, as the procedure is performed, the imaging device attached to the distal end of one of the articulated arms (e.g., stereoscopic endoscope, arthroscope, surgical microscope, and/or the like) may continue to take additional images of the patient's anatomy and/or one or more of the anatomical markers. In some examples, these additional images may be used to continuously track the positions and/or orientations of the one or more anatomical markers in the articulated arm coordinate system. In some examples, this tracking permits the computer-assisted surgical system to monitor the kinematic relationships between the computer-assisted medical device and the patient's anatomy as well as to monitor any changes in the positions and/or orientations of the patient's anatomy due to movement of the patient, physiological motions of the patient, and/or movement made to the patient's anatomy as part of the procedure (e.g., the setting of a bone, retraction of tissue, and/or the like). In some examples, the tracking of one or more of the anatomical markers may cease and tracking of others of the one or more anatomical markers may begin as the area of interest during the procedure changes.

At a process 460, the one or more anatomical markers are re-mapped to the pre-operative surgical plan. Using a process similar to process 445, the one or more anatomical markers tracked during process 455 are again mapped to the pre-operative plan so that any changes in the positions and/or orientations of the anatomical markers and the portions of the patient's anatomy to which they are attached are accounted for.

At a process 465, one or more medical tools are guided based on the one or more anatomical markers. In some examples, the various kinematic relationships of the computer-assisted medical device (e.g., kinematic relationships 370, 375, and/or 380) along with the patient to computer-assisted medical device kinematic relationship (e.g., the patient kinematic relationship 385) may be used to determine a motion plan and/or a suggested motion plan for the respective medical tools based on the surgical plan. In some examples, a medical tool to target kinematic relationship (e.g., medical tool to target kinematic relationship 390) may be determined by suitable application of the inverse and forward kinematic relationships. In some examples, the medical tool to target kinematic relationship may be used to quickly convert the position and orientation of the medical tool in its respective articulated arm coordinate system or vice versa to the intra-operative patient coordinate system so as to support positioning and alignment of the medical tool with the target while avoiding the no-fly zones.

In some embodiments, the computer-assisted medical device may provide hints and/or suggestions to help guide the one or more medical tools. In some examples, suggestions for the position and/or orientation of the one or more medical tools may be shown to the medical personnel as an overlay on the one or more images obtained during process 455 to track the one or more anatomical markers, the one or more pre-operative images loaded during process 405, and/or the one or more intra-operative images obtained during process 435. In some examples, one or more visual and/or audible cues may be provided to the medical personnel to guide the one or more medical tools to corresponding targets on or near the patient's anatomy. In some examples, the one or more visual cues may depict a conical and/or other shape converging to the desired position and/or orientation for each respective medical tool. In some examples, the visual cues may include depiction of a virtual rendition of each respective medical tool and a desired position and/or orientation of that medical tool. In some examples, haptic feedback may be used to direct the one or more medical tools to the desired positions and/or orientations.

In some embodiments, the one or more medical tools may be placed automatically. In some examples, motion planning may be used to automatically direct each of the medical tools to their desired position and/or orientation. In some examples, the motion planning may include planning a trajectory for each of the articulated arms to which the respective medical tools are attached. In some examples, the automatic placement may support a manual override control that allows medical personnel to abort the automatic placement of the one or more medical tools.

Method 400 may then continue by returning to process 455 to begin the tracking and guidance loop again. In some examples, process 455, 460, and 465 may implement an iterative loop allowing for continued monitoring and guidance of the medical tools and the patient's anatomy throughout the procedure.

As discussed above and further emphasized here, FIG. 4 is merely an example, which should not unduly limit the scope of the claims. One of ordinary skill in the art would recognize many variations, alternatives, and modifications. According to some embodiments, the anatomical markers may be attached to structures other than the patient's anatomy. In some examples, the anatomical markers may be affixed to the medical tools, the end effectors, and/or the articulated arms of the computer-assisted medical device to aid in observation of the positions and/or orientations of the medical tools, the end effectors, and/or the articulated arms in the same and/or different images used to observe the patient's anatomy.

According to some embodiments, an optional process to register the computer-assisted medical device to the patient table may also be included. In some embodiments, a table to medical device kinematic relationship, such as the table to device-base kinematic relationship 365, may be determined using a registration process between the patient table and the computer-assisted medical device. Methods and approaches for establishing the table to medical device kinematic relationship are described in greater detail in U.S. Patent Application No. 61/954,538, incorporated by reference above.

In some embodiments, additional control approaches may also be supported by the computer-assisted medical device while working with anatomical markers. In some examples, the computer-assisted medical device may monitor the patient table to allow for changes in position and/or orientation of the patient table. In some examples, the computer-assisted medical device may monitor the state of the table to medical device kinematic relationship (e.g., table to device-base kinematic relationship 365) and adjust the other kinematic relationships (e.g., kinematic relationships 370, 375, and/or 380) in order to keep the patient to computer-assisted medical device kinematic relationship constant and/or to automatically account for the movement of the patient table.

In some examples, this monitoring may also be performed through the tracking of the one or more anatomical markers during process 455.

Some examples of control units, such as control unit 280 may include non-transient, tangible, machine readable media that include executable code that when run by one or more processors (e.g., processor 285) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted medical device comprising:
a control unit comprising one or more processors;
a first articulated arm comprising one or more first joints;
a second articulated arm comprising one or more second joints;
a first imaging device mounted to a distal end of the first articulated arm; and
a medical tool mounted to a distal end of the second articulated arm;
wherein the control unit:
obtains one or more first images from a second imaging device intra-operatively during a procedure, the second imaging device using a first imaging modality;
determines first coordinates of one or more multi-modal anatomical markers relative to an anatomy of a patient based on content of the first images, wherein the one or more multi-modal anatomical markers are secured to the patient;
obtains one or more second images from the first imaging device using a second imaging modality intra-operatively during the procedure;
determines second coordinates of the one or more multi-modal anatomical markers relative to the medical tool based on content of the second images, wherein at least one of the one or more multi-modal anatomical markers includes a body comprising a first region observable by the first imaging modality and comprising a second region observable by the second imaging modality; and
registers the medical tool to the anatomy of the patient based on the first and second coordinates and kinematic models of the first and second articulated arms.

2. The computer-assisted medical device of claim 1, wherein the one or more multi-modal anatomical markers includes a plurality of anatomical markers, wherein each anatomical marker of the plurality of anatomical markers has a shape different than a shape of each other anatomical marker of the plurality of anatomical markers to identify each anatomical marker.

3. The marker of claim 2, wherein the shape of at least one of the anatomical markers of the plurality of anatomical markers is selected from a group consisting of a sphere, a circular cylinder, a rectangular box, a star-shaped cylinder, a polygonal cylinder, a letter, a number, a barcode pattern, and a chessboard pattern.

4. The computer-assisted medical device of claim 1, wherein the first imaging modality is x-ray.

5. The computer-assisted medical device of claim 1, wherein the second imaging modality is stereoscopic fluorescence imaging.

6. The computer-assisted medical device of claim 1, wherein the control unit further adjusts a position and an orientation of the first imaging device from which the second images are obtained so that the one or more multi-modal anatomical markers are within a field of view of the first imaging device.

7. The computer-assisted medical device of claim 1, wherein the first and second imaging modalities obtain their images without using light in a visible spectrum.

* * * * *